United States Patent [19]
Sweeney et al.

[11] 4,018,657
[45] Apr. 19, 1977

[54] SEPARATION OF HYDROCARBON MIXTURES BY ALKYL DISPLACEMENT

[75] Inventors: William A. Sweeney, Larkspur; Milutin Simic, Novato, both of Calif.

[73] Assignee: Chevron Research Company, San Francisco, Calif.

[22] Filed: Apr. 1, 1976

[21] Appl. No.: 672,704

[52] U.S. Cl. .................................. 203/38; 203/65; 203/84; 260/671 R; 260/677 A
[51] Int. Cl.² ...................... C07C 11/02; B01D 3/34
[58] Field of Search ...................... 203/38, 65, 84; 260/677 A, 671 R, 672 R, 671 A

[56] References Cited
UNITED STATES PATENTS

| 2,265,583 | 12/1941 | Stevens et al. | 260/677 A |
| 3,344,202 | 9/1967 | Ziegenhain | 260/677 R |
| 3,651,165 | 3/1972 | Horie | 260/677 A |
| 3,655,520 | 4/1972 | Harkins | 203/38 |
| 3,679,550 | 7/1972 | Orwoll | 203/38 |
| 3,751,509 | 8/1973 | Liakumovich et al. | 260/677 A |

Primary Examiner—Wilbur L. Bascomb, Jr.
Attorney, Agent, or Firm—J. A. Buchanan, Jr.; John Stoner, Jr.; W. Keith Turner

[57] ABSTRACT

A process for separating mixtures of close boiling, high-molecular weight alkenes and alkanes which employs phenoxide-catalyzed alkyl displacement.

6 Claims, 1 Drawing Figure

CONTINUOUS PROCESS FOR SEPARATING HYDROCARBON MIXTURES

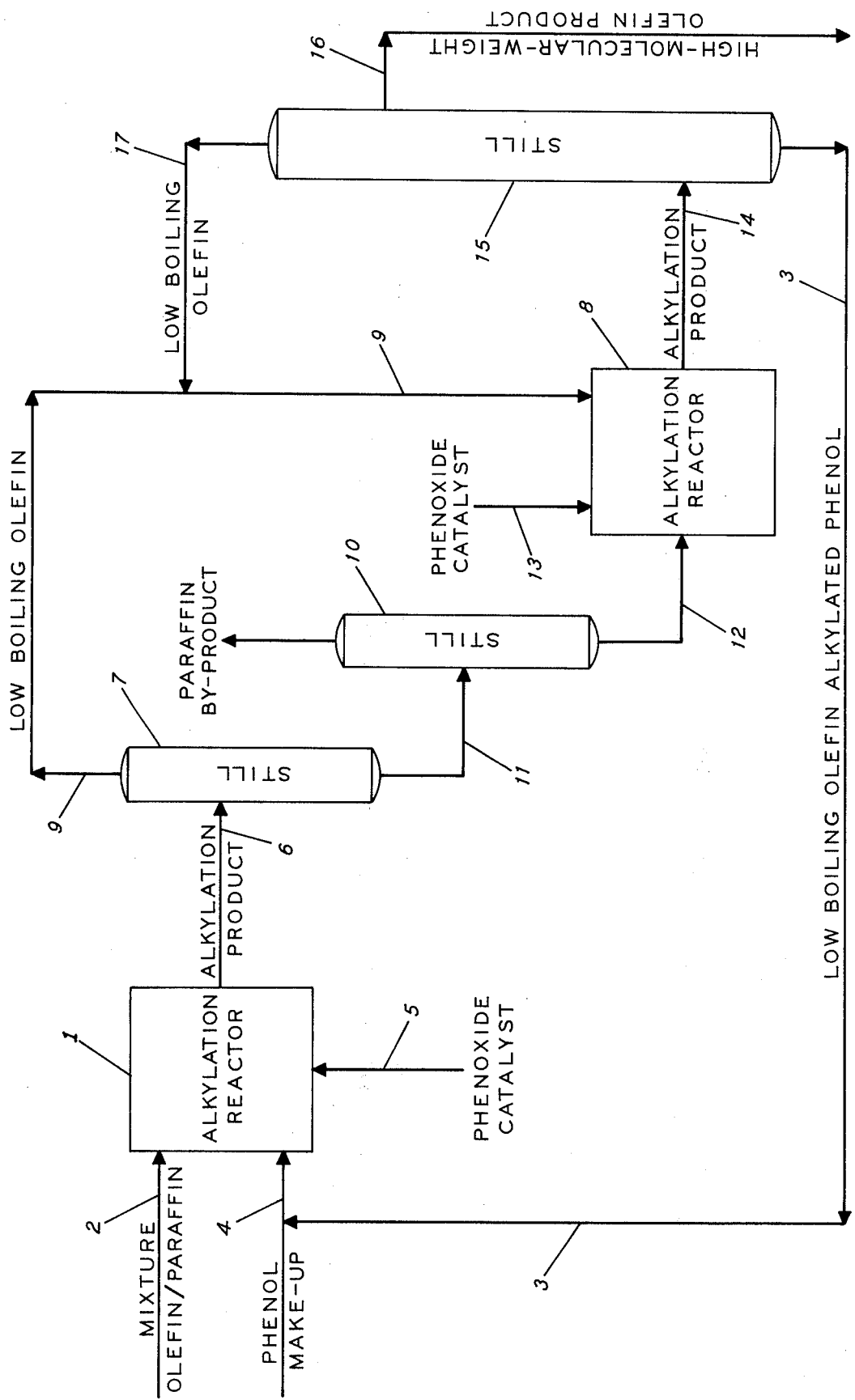

SEPARATION OF HYDROCARBON MIXTURES BY ALKYL DISPLACEMENT

BACKGROUND OF THE INVENTION

The present invention relates to a process for separating mixtures of high-molecular-weight olefins and normal paraffins. In particular, the process of this invention employs phenoxide catalyzed olefin alkylation of phenols as a means of harboring and regenerating high-molecular-weight olefins.

A valuable application of the separation process of this invention lies in the area of biodegradable detergents.

High-boiling linear olefins containing at least about 8 carbon atoms are useful in the synthesis of biodegradable surfactants. While several processes are available for dehydrogenating normal paraffins to prepare linear olefins, these processes actually result in the formation of a mixture of paraffins and olefins. For example, U.S. Pat. No. 3,248,451, granted Apr. 26, 1966, describes the use of a cobalt molybdate compound supported on alumina to catalyze the vapor phase dehydrogenation of long-chain normal paraffins. Despite the improved yields reported, the product of the cobalt molybdate process contained significant amounts of paraffin.

While, in some cases, the paraffin-diluted olefins produced by dehydrogenation can be used as such; in many cases pure olefins are required. For instance, olefin sulfonation to prepare detergent compounds having particularly desirable biodegradability and efficacy employs pure olefins. As a consequence of the need for pure olefin feedstocks several processes have been suggested for separating mixtures of high-molecular-weight olefins and normal paraffins. The most notable of these separations employ molecular sieves or selective extraction. For instance, U.S. Pat. No. 3,767,724 granted Oct. 23, 1973, describes the use of extractive crystallization to separate acyclic hydrocarbon mixtures of alkenes and alkanes; U.S. Pat. No. 3,355,509 granted Nov. 28, 1967, and British Pat. No. 1,107,307 describe the separation of acyclic hydrocarbon mixtures by molecular sieves; and *Petroleum Processing*, August 1949, describes the use of cyclic adsorption to separate hydrocarbon mixtures. In many instances even these procedures do not successfully separate a 100% pure olefin fraction.

Accordingly, there is a continuing need for a process for separating mixtures of high-molecular-weight olefins and normal paraffins.

SUMMARY OF THE INVENTION

It has been found that close boiling mixtures comprising high-molecular-weight olefins and paraffins can be separated by a process comprising the steps of:

1. contacting a paraffin-diluted high-molecular-weight olefin mixture with a phenolic compound in the presence of a phenoxide alkylation catalyst under conditions effective to cause olefin alkylation between the high-molecular-weight olefin and the phenol to prepare a high-molecular-weight alkylphenol;
2. recovering the high-molecular-weight alkylphenol;
3. contacting the high-molecular-weight alkylphenol with an excess of low-molecular-weight olefin in the presence of a phenoxide alkylation catalyst under conditions effective to regenerate the high-molecular-weight olefin; and
4. recovering paraffin-free high-molecular-weight olefin.

In a preferred embodiment of the present process the paraffin-diluted high-molecular-weight olefin feedstock comprises substantially linear olefins.

BRIEF DESCRIPTION OF THE DRAWING

The several features of the present process will become more readily apparent from the following detailed description of the invention taken in conjunction with the accompanying drawing. The drawing illustrates a block-flow diagram of a preferred separation process employing olefin and alkylphenol recycle.

DETAILED DESCRIPTION OF THE INVENTION

The essential steps of the process of this invention are described by the reaction sequence

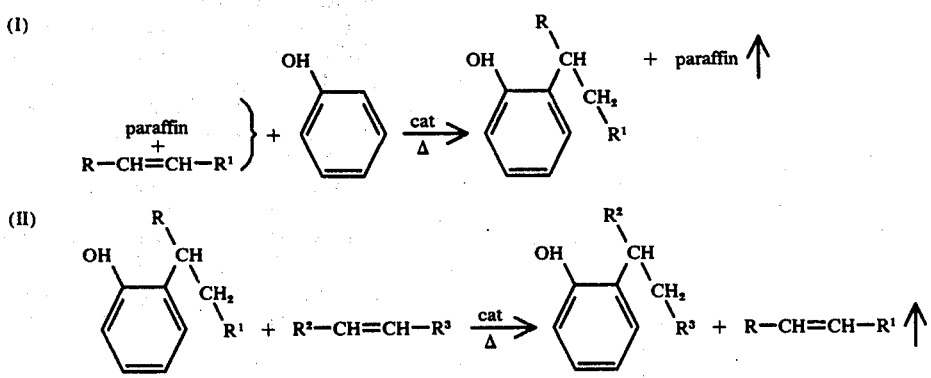

wherein $R-CH=CH-R^1$ is a high-molecular-weight olefin; $R^2-CH=CH-R^3$ is a low-molecular-weight olefin containing at least two fewer carbon atoms than the high-molecular-weight olefin; and R, $R^1$, $R^2$ and $R^3$ are hydrogen or alkyl.

The range of molecular weights of the olefin/paraffin mixtures suitable for use in the process of this invention is very wide. The process can be employed with olefin/paraffin mixtures comprising hydrocarbons having as few as 4 carbon atoms or as high as 100 carbon atoms and beyond. However, for practical purposes suitable feedstock mixtures will comprise olefins and paraffins having from about 8 to about 40 carbon atoms.

In the first step of the present process, a close-boiling mixture comprising paraffin-diluted high-molecular-weight olefins and paraffins is contacted with a phenolic compound in the presence of a phenoxide alkylation catalyst under conditions effective to cause olefin alkylation between the phenol and the high-molecular-weight olefin. As used herein, the term "high-molecular-weight olefin" encompasses olefins containing at least about 4 carbon atoms, preferably at least 8 carbon atoms, which are essentially free of other reactive moieties.

It has been found that the conditions of phenolic alkylation described above will similarly effect an alkyl displacement between the high-molecular-weight olefin and low-molecular-weight alkylphenol. This reaction is described by the reaction formula:

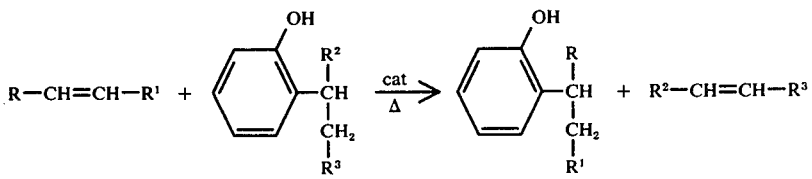

As can be appreciated from Formula I, above, the olefin alkylation reaction employed in the first step of the present process serves as a means to harbor the high-molecular-weight olefin as an alkyl moiety. The olefin is subsequently freed again in Step 3. Accordingly, the conditions of the catalytic reactions must be controlled to insure that the olefin is not destroyed or that side-reactions such as polymerization and disproportionation do not occur. For example, when substantially linear olefins are being separated for use in biodegradable surfactants the linear nature of the olefin must not be destroyed. It has been found that by employing select phenoxide catalysts described by the molecular structure

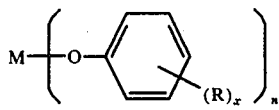

wherein M is aluminum or magnesium metal, $n$ is the valence of the metal, R is lower alkyl, and X is 0, 1 or 2, the side reactions of skeletal isomerization, polymerization, etc., will not occur; in particular, substantially linear olefins will be recovered as such. Lower alkyl groups are those having from 1 to about 4 carbon atoms. The phenoxide catalyst will generally correspond to the phenolic compound being used to harbor the olefin during the separation since the metal moiety is free to exchange phenolic groups under the process conditions.

The first step alkylation is carried out under the usual liquid alkylation conditions, in particular, temperatures ranging from about 150° to about 320° C, preferably from about 220° to about 300° C. The reaction proceeds in the liquid phase so that sufficient pressure must be employed to maintain liquid conditions at the temperature of reaction.

While phenol, per se, is of course a suitable phenolic compound for use in the first step alkylation, it is also possible to employ low-molecular-weight alkylphenols. The phenolic compound must have an alkylatable position free or available by alkyl displacement to be useful in this process. It is preferable that this be a position ortho to the hydroxide group. It is believed advantageous to block the para position and one ortho position with a methyl group; i.e., by the use of 2,4-dimethyl phenol. When more than one phenolic alkylation position is available some of the product from Step 1 or Step 3 may contain more than one entering alkyl group.

wherein R, $R^1$, $R^2$ and $R^3$ are hydrogen or alkyl and $R^2$—CH=CH—$R^3$ contains at least two less carbon atoms than R—CH=CH—$R^1$. Therefore, the phenolic compound employed in Step 1 may contain replaceable alkyl substituents which have at least two fewer carbon atoms that the olefin to be recovered. As will be more thoroughly detailed hereinafter, the use of a low-molecular-weight alkylphenol is preferred in continuously designed processes.

In the second step of the present invention process the reaction product of the first step comprising paraffin, high-molecular-weight alkylphenol, and (where an alkylphenol is employed as an initial reactant) low-molecular-weight olefin is heated under conditions sufficient to separate the reaction product into paraffin, olefin, and alkylphenol fractions. Separation can be achieved by employing conventional stripping and distillation techniques. For example, the low boiling displaced olefin can be stripped off and paraffin can be distilled overhead to leave alkylphenol as a bottoms product. The removal of low-molecular-weight olefin could be accomplished during Step 1 by allowing the olefin to distill overhead from the reaction vessel, thereby improving the rate of alkyl displacement. However, Step 2 would still be required to remove the high-molecular-weight paraffins.

In the third step of the present process, illustrated by Formula II above, the recovered high-molecular-weight alkylphenol, which is now separated from the paraffins fraction of the initial olefin-paraffin mixture, is contacted with an excess of low-molecular-weight olefin in the presence of a phenoxide catalyst, as described above, under conditions effective to regenerate the high-molecular-weight olefin and low-molecular-weight alkyl phenol. As used herein the term "low-molecular-weight olefin" encompasses olefins containing at least two less carbon atoms than the lowest-molecular-weight high-molecular-weight olefin. For example, if the process of this invention were employed to separate a mixture of $C_{12}$ and higher-molecular-weight olefins from normal paraffins, suitable low-molecular-weight olefins must contain no greater than 10 carbon atoms.

The reaction employed in the third step is an alkyl displacement reaction in which the low-molecular-weight olefin displaces the linear high-molecular-weight alkyl of the alkylphenol to prepare a low-molecular-weight alkylphenol and regenerate a high-molecular-weight linear olefin. The conditions of reaction are as described in step 1.

As a final step the regenerated high-molecular-weight olefin is recovered from the reaction product of Step 3 comprising olefin and alkylphenol. Conventional distillation may be employed to recover olefin as an overhead product. In Steps 2 and 4 distillation is described as the preferred physical method for separating the phenolic compounds from lower-boiling olefins and paraffins. Other physical methods of separation such as extraction or adsorption are also contemplated. Another more preferred embodiment of this invention employs a reactive polymeric phenolic compound which is separated by decanting or filtration.

The present invention is particularly advantageous where continuous processing is employed. In particular, by selecting a phenolic compound having a low-molecular-weight alkyl moiety it is possible to recycle both the phenolic compound and the low-molecular-weight olefin. The drawing is a block-flow diagram illustrating a preferred continuous process employing phenol and olefin recycle. Referring to the drawing, reactors 1 and 8 are pressure vessels containing a heating means, a temperature control means, and a means for mixing. Fresh feedstock in line 2 is continuously fed into reactor 1. At the same time recycled low-molecular-weight alkylphenol in line 3 is combined with make-up alkylphenol in line 4, and then continuously charged to reactor 1. Phenoxide catalyst is charged to reactor 1 through line 5. Reactor 1 is maintained within the process limits discussed above. The crude reaction product comprising low-molecular-weight olefins, high-molecular-weight linear alkylphenol, and paraffin is continuously removed from reactor 1 through line 6, and passed into still 7. Still 7 is operated under conditions sufficient to vaporize low-boiling olefin which is recycled to reactor 8 through line 9. The bottoms from still 7 is continuously removed and passed to still 10 through line 11. Still 10 is operated under conditions sufficient to vaporize paraffin contaminate which is recovered as a by-product. The bottoms from still 10 comprising high-molecular-weight linear alkylated phenol is continuously removed and passed through line 12 to reactor 8. Phenoxide catalyst is charged to reactor 8 through line 13. Reactor 8 is maintained within the process limits discussed above. The crude reaction product comprising low-molecular-weight alkylphenol and high-molecular-weight linear olefins is continuously removed from reactor 8 through line 14, and passed into still 15. Still 15 is operated under conditions sufficient to recover high-molecular-weight linear olefins which are continuously removed from still 15 through line 16. Excess low-molecular-weight olefins are continuously removed from still 15 through line 17, and are combined with recycled olefin in line 9. Low-molecular-weight alkylphenol is continuously removed from still 15 through line 3 and combined with make-up phenol in line 4.

In accordance with the drawing, the present invention encompasses a continuous process for separating high-molecular-weight substantially linear olefins from mixtures of olefins and paraffins comprising the steps of: 1 contacting a paraffin-diluted high-molecular-weight substantially linear olefin with a low-molecular-weight alkylphenol in the presence of a phenoxide alkylation catalyst in a first reaction zone under conditions effective to cause alkyl displacement of the low-molecular-weight alkylphenol to prepare a reaction product comprising paraffin, low-molecular-weight olefins and high-molecular-weight substantially linear alkylphenols; 2 separating olefin from the reaction product of step 1; 3 separating paraffins from the residue of step 2; 4 contacting the high-molecular-weight alkylphenol residue of step 3 with excess low-molecular-weight olefin in the presence of a phenoxide alkylation catalyst in a second reaction zone under conditions effective to cause alkyl displacement of the high-molecular-weight alkylphenol to prepare a reaction product comprising excess low-molecular-weight olefin, high-molecular-weight substantially linear olefin, and low-molecular-weight alkylphenol; 5 separating excess low-molecular-weight olefin from the reaction product of step 4; 6 separating low-molecular-weight alkylphenol from the residue of step 5; 7 recovering paraffin-free high-molecular-weight substantially linear olefin; 8 recycling low-molecular-weight olefin from steps 2 and 5 to the second reaction zone of step 4; and 9 recycling low-molecular-weight alkylphenol from step 6 to the first reaction zone of step 1.

EXAMPLES

In the following example a mixture of olefins and paraffins containing from 17 to 20 carbon atoms was separated using the process of this invention. The mixture comprised an average of about 9.8% olefin, and was prepared by dehydrogenation of a silica gel-treated $nC_{17}$–$C_{20}$ wax. Dehydrogenation was conducted using the platinum-lithium-tin alumina supported catalyst described in U.S. Pat. No. 3,531,543. Typical conditions of dehydrogenation are summarized in Table I below.

TABLE I

FEED
    A silica gel-treated $C_{17}$–$C_{20}$ wax having a density of 0.770 and a molecular weight of 269.
CATALYST
    0.5% platinum, 0.5% tin, 0.1% lithium on an alumina support
REACTOR
    Inside diameter 0.394 cm.
    Catalyst volume 3.0 cc.
    Void volume 2.1 cc.
    Catalyst feed length 18.0 cm.
    Catalyst weight 2.46 gm.
RUN CONDITIONS
    Liquid space velocity 39.4/hour
    Pressure 20.0 psig.
    Temperature 830° F.
    Hydrogen-to-hydrocarbon molar ratio 15.6:1
    Contact time 0.09 sec
    Conversion 9.8% by weight of paraffin

EXAMPLE

Separation of $nC_{17}$–$C_{20}$ Paraffin Olefin Mixture

Three phenol alkylation runs were made with dilute linear $nC_{17}$–$C_{20}$ olefin prepared according to the procedure described above. In each run the phenol and aluminum metal catalyst were charged to an autoclave equipped with heating and mixing means. The temperature was increased to about 170° C and pressure increased to about 65 psig. The vessel was held under these conditions for about one hour to form the phenoxide at which time the temperature was lowered and the vessel was vented to release the hydrogen formed. About 8000 g of the 9.8% olefin mixture was then added. The temperature was then increased to 290° C and held for about 6 hours. Over-all conditions and results for the three runs are summarized in Table II below.

TABLE II

| No. | Charge[1] Phenol, Mole | Olefin,[2] Mole | Aluminum, g. At. | Conditions Temp., °C | Time, Hr | Olefin Conversion Total, % | Yield Distillate LAP[5] Based on n-Paraffin Conversion, % | Crude Alkylate Composition Phenol, % | Paraffin, % | LAP, % | Bottoms, % |
|---|---|---|---|---|---|---|---|---|---|---|---|
| 1 | 10 | 1 | 0.2 | 290 | 6 | 95 | 84 | 21.7 | 69.6[3] | 7.8 | 0.9 |
| 2 | 10 | 1 | 0.2 | 290 | 6 | 96 | 85 | 20.7 | 70.0[3] | 8.4 | 0.9 |
| 3 | 10 | 1 | 0.4 | 290 | 8 | 93 | 77 | 21.0 | 69.5[4] | 7.8 | 1.7 |

[1]Alkylations No. 1 and 2 were run in 5-gallon autoclave using the following charge:
Phenol, g  2540.0
Dehydrogenation Product, g  8000.0
Aluminum, g  16.0
Alkylation No. 3 was run with 32 g aluminum.
[2]Charged as 9.8% olefin in paraffin.
[3]Contains 0.5% olefin.
[4]Contains 0.7% olefin.
[5]Linear Alkyl Phenol.

A 44 gr sample of $C_{17}$–$C_{20}$ monoalkylphenol, obtained in accordance with the above procedure by alkylation of a paraffin-diluted olefin, was reacted with 101 g of 1-dodecene and 44 gm. of aluminum phenoxide catalyst as follows.

Aluminum phenoxide was formed by charging 0.5 gm. of aluminum to a four-necked reaction flask, adding 15.8 gm. of phenol and 44 g of $C_{17}$–$C_{20}$ monoalkylphenol, and heating at about 180° C for 30 minutes until all aluminum was dissolved. Excess phenol, about 9 g, was distilled off, and 101 g of 1-dodecene were added. The contents were then heated at reflux, about 240° C., for about 24 hours. Tables III, IV and V summarize the results.

TABLE III
PRODUCT COMPOSITION OF THE ALKYL DISPLACEMENT REACTION

| Compound[1] | Reaction at 240° C, Hr 18 | 20 | 26 |
|---|---|---|---|
| $C_{12}$-Olefin, %[2] | 45.5 | 43.0 | 43.5 |
| $C_{17}$–$C_{20}$ Olefin, % | 7.2 | 8.0 | 9.2[4] |
| $C_{12}$-Monoalkylphenol, % | 0.8 | 0.9 | 1.9 |
| $C_{12}$Dimer, % | | | 0.3 |
| $C_{17}$–$C_{20}$ Monoalkylphenol,[3] % $C_{12}$ Dialkylphenol, % | 22.0 | 23.2 | 23.4 |
| High Molecular Weight Compound, % | 24.4 | 25.1 | 22.2 |

[1]Listed in order of elution.
[2]All percentages from integration counts.
[3]Most of the peaks covered by $C_{12}$dialkylphenol.
[4]Corresponds to 30% of the original olefin present in the $C_{17}$–$C_{20}$ monoalkylphenol.
Analysis: GC on 10-ft OV-17, programmed at 10° C/min. from 100–310° C.

TABLE IV
CARBON DISTRIBUTION IN FEED OLEFIN AND IN DEALKYLATED OLEFIN

| | Starting Olefin, % | Dealkylated Olefin, % |
|---|---|---|
| $C_{17}$ | 23.6 | 26.0 |
| $C_{18}$ | 30.0 | 33.0 |
| $C_{19}$ | 27.8 | 27.0 |
| $C_{20}$ | 18.6[1] | 14.0 |

[1]$C_{20}$ component contains about 25° $C_{20}$ paraffins.

TABLE V
$C_{19}$ISOMER DISTRIBUTION IN FEED OLEFIN AND IN DEALKYLATED OLEFIN

| Feed Olefin | | Dealkylated Olefin | |
|---|---|---|---|
| Isomer | % | Isomer | % |
| cis-2 | 7.1 | cis-2 | 16.9 |
| trans-2 | 27.7 | trans-2 | 17.3 |
| cis-3 | 6.4 | cis-3] | 6.3 |
| trans-3 | 23.6 | trans-3 and -4 | 29.9 |
| Others | 27.2 | Others | 19.0 |
| 1-Olefin | 2.0 | | |
| Paraffin | 6.0 | cis-7, -8, -9 | 8.0 |
| | | Diene | 2.6 |

About 30% of the $C_{17}$–$C_{20}$ alkyl chain dealkylated after 26 hours at reflux temperature. The composition of the reaction product did not change significantly after 18 hours. The dealkylated product was about the same carbon distribution as the original olefin used to prepare the $C_{17}$–$C_{20}$ alkylphenol (Table IV). The double bond distribution is about the same in the two olefins as seen from the distribution of the 2- and 3-isomers in the $C_{19}$ olefin (Table V).

A similar procedure employing sulfuric acid-treated clay (clay treated with 10 wt. % of 95% $H_2SO_4$) as the catalyst did not promote dealkylation.

What is claimed is:

1. A process for separating a close-boiling mixture comprising high-molecular-weight olefins and paraffins which comprises the steps of:
   1. contacting a paraffin-dilute high-molecular-weight olefin mixture with a phenolic compound in the presence of a phenoxide alkylation catalyst under conditions effective to cause olefin alkylation between the high-molecular-weight olefin and the phenol to prepare a high-molecular-weight alkyl phenol;
   2. recovering the high-molecular-weight alkyl phenols;
   3. contacting the high-molecular-weight alkyl phenol with an excess of low-molecular-weight olefin in the presence of a phenoxide alkylation catalyst under conditions effective to regenerate the high-molecular-weight olefin; and
   4. recovering paraffin-free high-molecular-weight olefin.

2. A process according to claim 1 wherein said mixture comprises $C_8$ to $C_{40}$ olefins.

3. A process according to claim 2 wherein said olefins are substantially linear.

4. A process according to claim 1 wherein said phenoxide alkylation catalyst is an aluminum triphenoxide.

5. A process according to claim 1 wherein Steps 2 and 4 employ distillation.

6. A continuous process for separating a close-boiling mixture comprising high-molecular-weight linear olefins and paraffins which comprises the steps of:
1. contacting a paraffin-dilute high-molecular-weight substantially linear olefin with a low-molecular-weight alkyl phenol in the presence of a phenoxide alkylation catalyst in a first reaction zone under conditions effective to cause alkyl displacement of the low-molecular-weight alkyl phenol to prepare a reaction product comprising paraffin, low-molecular-weight olefins and high-molecular-weight substantially linear alkyl phenols;
2. separating olefin from the reaction product of step 1;
3. separating paraffins from the residue of step 2;
4. contacting the high-molecular-weight alkyl phenol residue of step 3 with excess low-molecular-weight olefin in the presence of a phenoxide alkylation catalyst in a second reaction zone under conditions effective to cause alkyl displacement of the high-molecular-weight alkyl phenol to prepare a reaction product comprising excess low-molecular-weight olefins, high-molecular-weight substantially linear olefin, and low-molecular-weight alkyl phenol;
5. separating excess low-molecular-weight olefin from the reaction product of step 4;
6. separating low-molecular-weight alkyl phenol from the residue of step 5;
7. recovering paraffin-free high-molecular-weight substantially linear olefin;
8. recycling low-molecular-weight olefin from steps 2 and 5 to the second reaction zone of step 4; and
9. recycling low-molecular-weight alkyl phenol from step 6 to the first reaction zone of step 1.

* * * * *